United States Patent
Sørensen et al.

(10) Patent No.: US 9,084,436 B2
(45) Date of Patent: *Jul. 21, 2015

(54) METHOD OF PREPARING FIBRE-CONTAINING PECTIN PRODUCT AND PECTIN PRODUCTS HEREOF

(75) Inventors: Ole Bandsholm Sørensen, Give (DK); Peter Fromholt Larsen, Højbjerg (DK)

(73) Assignee: KMC Kartoffelmelcentralen AMBA, Brande (DK)

( * ) Notice: Subject to any disclaimer, the term of this patent is extended or adjusted under 35 U.S.C. 154(b) by 983 days.

This patent is subject to a terminal disclaimer.

(21) Appl. No.: 12/669,949

(22) PCT Filed: Aug. 29, 2008

(86) PCT No.: PCT/DK2008/050216
§ 371 (c)(1),
(2), (4) Date: Jun. 10, 2010

(87) PCT Pub. No.: WO2009/026936
PCT Pub. Date: Mar. 5, 2009

(65) Prior Publication Data
US 2010/0247582 A1 Sep. 30, 2010

(30) Foreign Application Priority Data
Aug. 29, 2007 (DK) .......................... PA 2007 01228

(51) Int. Cl.
A23L 1/308 (2006.01)
A23L 1/0524 (2006.01)
A23L 1/212 (2006.01)
A23L 1/305 (2006.01)
A61K 8/02 (2006.01)
A61K 8/06 (2006.01)
A61K 8/97 (2006.01)
A61Q 19/00 (2006.01)
C08B 37/00 (2006.01)
C08H 8/00 (2010.01)
C08L 5/06 (2006.01)
C08L 99/00 (2006.01)

(52) U.S. Cl.
CPC ............ *A23L 1/3081* (2013.01); *A23L 1/0524* (2013.01); *A23L 1/2126* (2013.01); *A23L 1/3055* (2013.01); *A61K 8/027* (2013.01); *A61K 8/064* (2013.01); *A61K 8/97* (2013.01); *A61Q 19/00* (2013.01); *C08B 37/0048* (2013.01); *C08H 8/00* (2013.01); *C08L 5/06* (2013.01); *C08L 99/00* (2013.01); *A23V 2002/00* (2013.01)

(58) Field of Classification Search
None
See application file for complete search history.

(56) References Cited

U.S. PATENT DOCUMENTS

| 2,754,214 A | 7/1956 | Leo et al. |
| 5,567,462 A | 10/1996 | Ehrlich |
| 7,833,558 B2 * | 11/2010 | Larsen et al. ................. 426/577 |
| 2006/0142158 A1 * | 6/2006 | Nonomura .................... 504/101 |

FOREIGN PATENT DOCUMENTS

| JP | 61089205 A | 5/1986 |
| JP | 11009173 A | 1/1999 |
| RU | 2 282 636 C1 | 8/2006 |
| SU | 1675303 A1 | 9/1991 |
| WO | WO 99/10384 A1 | 3/1999 |
| WO | WO 00/58367 A1 | 10/2000 |
| WO | WO 2005/003178 A1 | 1/2005 |
| WO | WO 2005003178 A1 * | 1/2005 |

OTHER PUBLICATIONS

Krall, Sandra M. et al.; "Pectin Hydrolysis: Effect of Temperature, Degree of Methylation, pH, and Calcium on Hydrolysis Rates," 1998, ACS, Journal of Agriculture and Food Chemistry, vol. 46, No. 4, pp. 1311-1315.*
Fang, Yapeng et al.; "Binding behavior of calcium to polyuronates: Comparison of pectin with alginate," 2008, Elsevier; Carbohydrate Polymers, vol. 72, pp. 334-341.*
Daas, Piet J. H. et al., "Analysis of Partially Methly-Esterfied Galacturonic Acid Oligomers by High-Performance Anion-Exchange Chromatography and Matrix-Assisted Laser Desorption/Ionization Time-of-Flight Mass Spectrometry" Analytical biochemistry, 1998, pp. 195-202, vol. 257.
Melton, Laurence D. et al., "Determining the Degree of Methylation and Acetylation of Pectin" Current Protocols in Food Analytical Chemistry, 2001, pp. E3.4.1-E3.4.6.
International Search Report for PCT/DK2008/050216 dated Feb. 2, 2009.

* cited by examiner

*Primary Examiner* — Suzanne Ziska
*Assistant Examiner* — Ivan Greene
(74) *Attorney, Agent, or Firm* — Stephen G. Anderson; GrayRobinson, P.A.

(57) ABSTRACT

The present invention relates to a method for providing a fiber-containing pectin product from a plant material. The method comprises the steps of: (i) providing a plant material comprising pectin, where said pectin is having a degree of esterification of 55% or less, (ii) adding an acidic aqueous solution to the pectin containing plant material obtained in step (i) and providing a suspension of the plant material, where the suspended plant material provides an in situ system by swelling the plant material under conditions where the pectin is kept within the plant material, and (iii) obtaining the fiber-containing pectin product from the suspension provided in step (ii), wherein the plant material is substantially depleted from divalent cations.

28 Claims, No Drawings

US 9,084,436 B2

METHOD OF PREPARING FIBRE-CONTAINING PECTIN PRODUCT AND PECTIN PRODUCTS HEREOF

CROSS REFERENCE TO RELATED APPLICATIONS

This application claims the benefit and priority to and is a U.S. National Phase Application of PCT International Application Number PCT/DK2008/050216, filed on Aug. 29, 2008, designating the United States of America and published in the English language, which is an International Application of and claims the benefit of priority to Danish Patent Application No. PA 2007 01228, filed on Aug. 29, 2007. The disclosures of the above-referenced applications are hereby expressly incorporated by reference in their entireties.

FIELD OF THE INVENTION

The present invention relates to the field of preparing pectin and pectinacious products from a plant material. In particular, a novel method for providing novel fibre-containing pectin products as well as novel pectin products obtained from said fibre-containing pectin product is provided.

BACKGROUND OF THE INVENTION

In the industrial processing of plant materials, such as potatoes, tobacco or cacao, the fibrous mass obtained, is among the by-products isolated in huge quantities. Similar by-products or waste products are known from many other agriculturally based productions, e.g., sugar beet slices from the production of sugar from sugar beets, citrus peels and citrus pulp from the manufacture of juice and ethereal oils from citrus fruits, and pomace residues from cider production.

These plant by-products are often considered as waste products to be disposed in the most appropriate and most inexpensive way. However, it will be understood that there may be quite obvious advantages by further developing such plant by-products into products of more commercial value.

A common feature of these by-products is that they consist essentially of soluble and insoluble plant fibres, of which about 60-80% are dietary fibres, including three biopolymers: cellulose, hemicellulose and pectin. They are involved in the structure of all plant cell walls, which can be conceived as a cellulose-hemicellulose-pectin network in which pectin, apart from being a structural element, also constitutes the "concrete" imparting rigidity to the plant cells and adhesion function in the space between them. This complex structure in which pectin is attached to the other cell wall components by different types of bonds for instance hydrogen bonds and/or ionic interaction is often termed protopectin. Pectin, per se, can be obtained by controlled, acidic or alkaline hydrolytic extraction of protopectin.

Pectin is a polymer of extreme complexity, composed of a backbone(s) of units of α-D-galacturonic acid attached by α-1,4-glycoside bonds to form long chains of polygalacturonic acid. The homogalacturonic regions are interspersed with rhamnogalacturonic regions with 1,2 linked α-L-rhamnopyranosyl residues bearing different kinds and amounts of neutral sugar side chains. The galacturonic acid units are esterified with methanol to a varying degree and can be partly esterified with acetyl on the secondary hydroxyls. An industrial distinction is thus made between high-methoxylated-pectin having a degree of esterification (DE) of greater than 50% and low-methoxylated-pectin having a degree of esterification of less than 50%. The degree of esterification is defined as the number of methyl-esterified galacturonic acid units expressed as a percentage of the total galacturonic acid units in the pectin molecule.

In pectin from some types of plant material, e.g. potatoes and sugar beets, a varying part of the galacturonic acid units may, in addition, have acetyl groups located on C-2 and C-3 positions, expressed as the degree of acetylation (DAc). DAc is defined, analogous to the degree of esterification, as the number of acetylated galacturonic acid units as a percentage of all galacturonic acid units.

Neutral sugars, such as galactose, glucose, rhamnose, arabinose and xylose, may also be part of the pectin polymer as side-chains to or as members in the polygalacturonic acid chain.

Hemicellulose is a heterogeneous group of polysaccharides containing several kinds of hexose and pentose sugars and, in some cases, residues of uronic acid. These polymers are classified according to the type of sugar residues being dominant and are individually referred to as xylanes, arabinogalactans, glucomannans and so on.

Conventionally, methods for isolating pectin from a plant material are provided, where the plant material is suspended in an acidic solution having a pH around 1-3 at elevated temperature and/or long extraction times, whereby the pectin begin to disintegrate and is being extracted from the plant material. Subsequently the solid phase and the liquid phase may be separated and the pectin may be isolated/purified from the liquid phase.

Thus, U.S. Pat. No. 5,567,462 discloses a method of preparing pecto-cellulosic compositions and pectin from pectin-containing plant raw materials, such as citrus peels, sugar beet pulp, sunflower residues, and pomace residues. The method consists of treating the comminuted plant raw materials with an acid, e.g., phosphoric or nitric acid, providing a pH in the range of pH 1-2.5. This treatment results in a suspension consisting of a solid phase containing cellulose components and a liquid phase containing dissolved pectin. The mixture is mashed, neutralised and finally dried to form pecto-cellulosic dry matter. The mashed mixture may also be separated into a solid and a liquid phase, which are neutralised individually and dried to give a pectin product and a pecto-cellulosic product.

In an alternative method as described in WO 05/003178 the plant material is used for providing an in situ system by swelling the plant material in a suspension comprising a salt which participates in keeping the structure of the plant material intact. When the plant material is in this swollen state the pectin can be chemically modified in a homogeneous manner. Subsequently, the modified pectin in combination with the remaining plant material may be worked up as a fibre containing pectin product or the pectin may be isolated providing a pectin product.

Thus, due to the highly industrial interests in the field of modifying pectin and in the production of different pectin products new methods are desirable for modifying and providing new pectin products.

SUMMARY OF THE INVENTION

Accordingly, the present invention relates in one aspect to a method for providing a fibre-containing pectin product from a plant material. The method comprises the steps of:
  (i) providing a plant material comprising pectin, where said pectin is having a degree of esterification of 55% or less,
  (ii) adding an acidic aqueous solution to the pectin containing plant material obtained in step (i) and providing a suspension of the plant material, where the suspended plant material provides an in situ system by swelling the plant material under conditions where the pectin is kept within the plant material, and (iii) obtaining the fibre-containing pectin product from the suspension provided in step (ii), wherein the plant material is substantially depleted from divalent cations.

In another aspect the present invention relates to a fibre-containing pectin product obtainable by a process according to the method of the present invention. In particular, the present invention relates to fibre-containing pectin products in the form of a plant material insoluble fibre product, a plant material soluble fibre product and a plant material activated fibre product.

In a further aspect the present invention relates to a method for providing a pectin product. The method comprising the steps of:

(i) providing a fibre-containing pectin product obtained by the present invention, (ii) adding an extraction medium to the fibre-containing pectin product providing an extraction suspension, (iii) adjusting the pH of the extraction suspension to a pH in the range of 1-12, (iv) adjusting the temperature of the extraction suspension to a temperature in the range of 0-120° C., and (v) isolating the pectin product from the aqueous phase of the extracting medium.

In yet an aspect the present invention relates to an isolated pectin product obtainable by a method described herein.

In still an aspect the present invention relates to a dietary fibre product obtainable by a method as described herein.

Furthermore, the present invention relates to a food product comprising the fibre-containing pectin products in the form of a plant material insoluble fibre product, a plant material soluble fibre product and a plant material activated fibre product, the isolated pectin product and/or the dietary fibre product as described herein.

In a further aspect the present invention relates to the use of a product provided according to the present invention for the encapsulation of, e.g., easily volatile lipid and/or water-soluble aromatic and colouring agents or by encapsulating micronutrients, flavouring agents, vitamins, etc., in the production of solid and liquid pharmaceutical compositions, including, e.g., tablets, suspensions, emulsions, etc. and as components in cosmetic products, such as perfumes, creams, and lotions, etc, as a viscosifying agent and/or an emulsifying agent, for fat replacement or for the replacement of tobacco or encapsulation of tobacco or for the encapsulation of tobacco for providing smokable and/or non-smokable products.

DETAILED DESCRIPTION OF THE PRESENT INVENTION

The purpose of the present invention is to provide a method for treating a plant material to provide a fibre-containing pectin product using an acidic aqueous solution under conditions where the pectin is kept within the plant material.

Pectins are complex molecules capable of forming strong inter/intra-chain interactions in the presence of divalent cations, such as calcium. The divalent cation is working as a binder between adjacent pectin molecules and can form so-called "egg-box" junction zones with galacturonic blocks of varying length.

In a preferred embodiment of the present invention it is of interest to washout the divalent cations or parts of the divalent cations, in particular the divalent calcium ion, present in and between the pectin molecules. The method comprises the steps of:

(i) providing a plant material comprising pectin, where said pectin is having a degree of esterification of 55% or less, (ii) adding an acidic aqueous solution to the pectin containing plant material obtained in step (i) and providing a suspension of the plant material, where the suspended plant material provides an in situ system by swelling the plant material under conditions where the pectin is kept within the plant material, and (iii) obtaining the fibre-containing pectin product from the suspension provided in step (ii).

In an embodiment of the present invention the plant material may be kept under conditions where the pectin is not dissolved and/or extracted from said plant material. Such conditions may be specific pH-values, specific temperature and time ranges, specific polarity of the solvent medium or any combination hereof, which secure the material remains intact under the isolation procedure.

In conventionally used methods, pectin (in particular high-ester-pectin) may dissolve when the pH is adjusted to a pH between 1 and 3 at elevated temperatures or at long extraction times. However, if the temperature is lowered and/or the processing time of the plant material is being reduced, the inventor of the present invention found that the internal bonds, such as hydrogen bonds, hydrophobic interactions and van der Waals bonds, not to mention the entanglement of the biopolymer with other nonsoluble macromolecules may be sufficiently strong to retain the pectin within the plant material. Even when the divalent cations have been liberated from the pectin molecules and reduced substantially compared to the starting material.

The conditions of the acidic aqueous solution may therefore be altered in such a way as to increase the interactions between the pectin molecules. Thereby increasing other internal bonds than ionic ones to become sufficiently strong to retain the pectin within the plant material in spite of the divalent cations no longer fulfil their function as cross-linkage material.

In the present context the term "washout" relates to the processing of the plant material by washing the plant material one or more times with an acidic aqueous solution. After each wash the plant material and the acidic aqueous solution are separated. In an embodiment of the present invention the separation may be performed by centrifugation, filtration (e.g. using filter pressing or belt pressing), decantation and/or a combination hereof.

In an embodiment of the present invention the suspended pectin containing plant material may be separated from the acidic aqueous solution in order to obtain the fibre-containing pectin product. In an embodiment of the present invention the separation may be performed by filtration, centrifugation, decanting, pressing (such as filter pressing or belt pressing) or a combination hereof.

Preferably, the method for providing the fibre-containing pectin product(s) according to the present invention may be conducted at a temperature below 80° C., such as below 70° C., e.g. 60° C. or below, such as 50° C. or below, e.g. 40° C. or below, such as 30° C. or below, e.g. 25° C. or below, such as in the range of 0-80° C., e.g. in the range of 0-70° C., such as in the range of 0-60° C., e.g. in the range of 0-50° C., such as in the range of 10-40° C., e.g. in the range of 15-35° C., such as in the range of 20-30° C.

The Plant Material

In the context of the present invention the terms "plant material" relates to any kind of plant material comprising pectin which may/can be used for preparing fibre-containing pectin products or pectin products. Furthermore, the term "plant material" relates to plant materials which has or has not been subjected to any kind of pre-treatment.

In an embodiment of the present invention the plant material may be obtained from a native vegetable material in a fresh or dried state.

In yet an embodiment of the present invention the plant material could be subjected to a pre-treatment before the acidic aqueous solution is added (step (ii)). Such pre-treatment could be a de-esterification treatment, an amidation treatment, any other kind of chemical or enzymatic treatment of either the plant material as such or a specific chemical or enzymatic treatment directed towards the pectin or any combination hereof. In a further embodiment of the present invention the pre-treatment of the plant material may also relate to separation of one or more component(s) or fraction(s) from the plant material, such as separation of the starch components from a potato leaving the potato pulp as the relevant plant material.

In a preferred embodiment of the present invention the plant material (pre-treated or not) has a degree of esterification of 55% or less, e.g. 50% or less, such as 45% or less, e.g. 40% or less, such as 35% or less, e.g. 30% or less, such as 20% or less.

Pectin consists mainly of galacturonic acid and galacturonic acid methyl ester units forming linear polysaccharide chains and is normally classified according to its degree of esterification. In the present context the term "degree of esterification" relates to the amount of carboxylic acid groups present in the polysaccharide chain which occurs as a methylester group instead.

In an embodiment of the present invention the plant material comprising pectin may be selected from the group consisting of potato, sugar beet, pomace residues from apples, peels or pulp from citrus fruits, such as lemon, orange, mandarin, lime, grapefruit, tobacco, cacao, sun flower, pumpkin, mango, tomato and Aloe Vera.

In a further embodiment of the present invention the plant material comprising pectin relates to the pulp obtained from potato, sugar beet, pomace residues from apples, peels or pulp from citrus fruits, such as lemon, orange, mandarin, lime, grapefruit, tobacco, cacao, sun flower, pumpkin, mango, tomato or Aloe Vera.

For the purpose of providing an increased effect of washing out the divalent cations the plant material may be subjected to comminution, pulverization, grinding, tearing or the like before the acidic aqueous solution is added. In particular, grinding of potatoes may be a suitable process for washing out the divalent cations.

The content of pectin in the plant material may differ for the individual plant materials, on dry matter basis, e.g., from about 30% to 40% by weight of pectin in citrus peels and from about 15% to 30% by weight of pectin in potato pulp.

The plant material may be subjected to a pre-treatment in order to obtain a plant material having a degree of esterification of 55% or less, which subsequently will be suited for the method described in the present invention. Preferred pre-treatments may be enzymatic treatment, preferably using pectinase or pectin esterase, such as NovoShape® or similar, or treatments like or similar to the method described in WO 2005/003178

Swelling

In an embodiment of the present invention the suspension of the plant material provides an in situ system by swelling the plant material in the acidic aqueous solution without, or substantially without, extracting pectin from the plant material.

Pectin may be essentially insoluble or no more than only poorly soluble in the acidic aqueous solution and the method of the invention may preferably be based on plant materials and conditions capable of providing a reaction system at the natural location of the pectin in the plant material, i.e., in situ.

In a preferred embodiment of the present invention the plant material is swelled in an acidic aqueous solution providing an in situ reaction system. In the present context the term "in situ reaction system" relates to a state in which the plant material act as the reaction chamber by being swelled and become permeable and thereby allowing the passage of e.g. reagents into the plant material and the passage of dissolved substances out of the plant material without dissolving the pectin polymer. The swelled "in-situ reaction system" is preferably is not a constant state of the plant material, but the plant material may return to its original packed state when the conditions are changed. In an embodiment of the present invention, the "in situ reaction system" makes it possible to subject the pectin polymer in the plant material to de-esterification treatment and/or amidation treatment within the plant material structure.

In yet an embodiment of the present invention during the treatment with the acidic aqueous solution, the protopectin in the plant material may be transformed into water-soluble pectins under such conditions that the water-soluble pectins formed remain in a non-diffusible state and aggregated with the insoluble plant cell constituents, such as cellulose and hemicellulose, and under which at least a part of the non-pectin-containing substances, such as, e.g., divalent cations, proteins, sugars or colorants may be removed.

The in situ system provided by the acidic aqueous solution and the plant material is to provide a state in which the plant material is essentially structurally intact allowing the passage of the acidic aqueous solution into the plant material and the passage of dissolved substances, such as divalent cations, out of the plant material. Since the cellulose-hemicellulose-pectin network may be to serve as a "container" in which the reaction occurs, the structure of this network is to be kept intact and must not be disintegrated as this may result in the formation of a suspension where pectin may be lost to the aqueous phase.

In a preferred embodiment of the present invention the acidic aqueous solution does not contain an organic solvent. Preferably, the aqueous solution is an inorganic aqueous solution.

In a preferred embodiment of the present invention swelling of the plant material provides a suspension in which the content of plant material dry matter is ranging from 1%-15% by weight, e.g. from 1%-10% by weight, typically from 4% to 8% by weight, such as 6% by weight.

The suspension of the pectin-containing plant starting material in the aqueous, saline solution occurs, while stirring, at a temperature below 80° C., such as below 70° C., e.g. 60° C. or below, such as 50° C. or below, e.g. 40° C. or below, such as 30° C. or below, e.g. 25° C. or below, such as in the range of 0-80° C., e.g. in the range of 0-70° C., such as in the range of 0-60° C., e.g. in the range of 0-50° C., such as in the range of 10-40° C., e.g. in the range of 15-35° C., such as in the range of 20-30° C. The temperatures in the range of 0-35 are often preferred because otherwise there is a risk that the plant material swells to quickly and the pectin starts to dissolve.

The time suitable for providing sufficient swelling of the plant material is being selected in order to obtain a structure which is sufficiently permeable and allowing passage of liquids and dissolved substances. In a preferred embodiment according to the present invention time the plant material is allowed to swell in the acidic aqueous solution, depending on the type and state of the pectin-containing plant material, from 1 to 120 minutes to obtain sufficient swelling and salt saturation of the pectin-containing plant material. In another embodiment the time selected is from 1-100 minutes, such as from 1-80 minutes, e.g. from 1-70 minutes, such as from 10-70 minutes, e.g. from 10-60 minutes, such as from 15-40 minutes, e.g. from 20-30 minutes, The time required for obtaining sufficient swelling and depletion of the divalent cations, such as calcium, depends, inter alia, on the physical dimensions of the pectin-containing plant starting material, which may be in the form of particles having an average particle size ranging from 1 mm or less and to parts with a maximum dimension of about 5 mm. The suspension of the present invention is provided with a pH value which is sufficiently low to washout the divalent cations. In an embodiment of the present invention the divalent cations may be selected from the group consisting of calcium ($Ca^{2+}$-ions), magnesium ($Mg^{2+}$-ions), strontium ($Sr^{2+}$-ions) or Barium ($Ba^{2+}$-ions).

In a preferred embodiment of the present invention the acidic aqueous solution has a pH value of 5 or less, such as pH 4 or less, e.g. pH 3 or less, such as pH 2 or less, e.g. pH 1, such as in the range of pH 1-5, e.g. in the range of pH 1-4, such as in the range of pH 2-4, e.g. in the range of pH 2-3. Preferably, the acidic aqueous solution has a pH value in the range of pH 1-2.

In an embodiment of the present invention the acidic aqueous solution in step (ii) does not comprise a salt. In a preferred embodiment of the present invention the acidic aqueous solution does not comprise a salt having a divalent cation.

PMIF

When treating the plant material according to the present invention a fibre-containing pectin product may be obtained which may be depleted or substantially depleted for divalent cations. In the present context the terms "depleted" and "substantially depleted" are used interchangeably and relates to fibre-containing pectin products having a content of divalent cations which is less than the content of divalent cations originally present in the plant material.

In a preferred embodiment of the present invention the plant material is depleted from divalent cations or substantially depleted from divalent cations. Preferably, the plant material is depleted from divalent cations or substantially depleted from divalent cations by removing at least 10% (w/w) of the divalent cations naturally present in the plant material, such as at least 20% (w/w) of the divalent cations, e.g. at least 30% (w/w) of the divalent cations, such as at least 40% (w/w) of the divalent cations, e.g. at least 50% (w/w) of the divalent cations, such as at least 60% (w/w) of the divalent cations, e.g. at least 70% (w/w) of the divalent cations, such as at least 80% (w/w) of the divalent cations, e.g. at least 90% (w/w) of the divalent cations, such as at least 95% (w/w) of the divalent cations, e.g. at least 98% (w/w) of the divalent cations.

The temperature during depletion of divalent cations from the plant material should be below 80° C., such as below 70° C., e.g. 60° C. or below, such as 50° C. or below, e.g. 40° C. or below, such as 30° C. or below, e.g. 25° C. or below, such as in the range of 0-80° C., e.g. in the range of 0-70° C., such as in the range of 0-60° C., e.g. in the range of 0-50° C., such as in the range of 10-40° C., e.g. in the range of 15-35° C., such as in the range of 20-30° C.

In a preferred embodiment of the present invention the fibre-containing pectin product obtained in step (iii) may be a plant material insoluble fibre product (PMIF-product).

In yet an embodiment of the present invention the PMIF-product may be capable of absorbing water. Preferably, at least 0.1 g water is absorbed per gram PMIF-product, such as at least 0.5 g water per gram PMIF-product, e.g. at least 1 g water per gram PMIF-product, such as at least 2 g water per gram PMIF-product, e.g. at least 3 g water per gram PMIF-product, such as at least 5 g water per gram PMIF-product, e.g. at least 10 g water per gram PMIF-product.

In an embodiment of the present invention the PMIF-product may be depleted for a divalent cation.

In a further embodiment of the present invention the divalent cation depleted from the fibre-containing pectin product and/or the PMIF-product may be calcium ($Ca^{2+}$-ions), magnesium ($Mg^{2+}$-ions), strontium ($Sr^{2+}$-ions) or Barium ($Ba^{2+}$-ions).

In another embodiment of the present invention the content of the cations, such as the divalent cation, present in the plant material and/or in the fibre-containing pectin product, is in a content after depletion of less than 50 mmol/kg dry matter, e.g. 40 mmol/kg dry matter or less, such as 30 mmol/kg dry matter or less, e.g. 25 mmol/kg dry matter or less, such as 20 mmol/kg dry matter or less, e.g. 15 mmol/kg dry matter or less, such as 10 mmol/kg dry matter or less, e.g. 5 mmol/kg dry matter or less, such as 1 mmol/kg dry matter or less, e.g. 0.5 mmol/kg dry matter or less.

After the PMIF-product has been obtained from the suspension the PMIF-product may be subjected to a (one or more) wash using water, such as demineralised water. The PMIF-product and the water may be separated to obtain a washed PMIF-product. The separation may be performed by filtration, centrifugation, decanting or a combination hereof.

In an embodiment of the present invention the PMIF-product has a pH value of 5 or less, such as pH 4 or less, e.g. pH 3 or less, such as pH 2 or less, e.g. pH 1, such as in the range of pH 1-5, e.g. in the range of pH 1-4, such as in the range of pH 1-2, e.g. in the range of pH 2-4, e.g. in the range of pH 2-3.

In yet an embodiment of the present invention the washed PMIF-product has a pH value of 6 or less, such as pH 5 or less, e.g. pH 4 or less, such as pH 3 or less, e.g. pH 2, such as in the range of pH 2-6, e.g. in the range of pH 2-5, such as in the range of pH 2-4, e.g. in the range of pH 3-4, e.g. in the range of pH 2-3.

The PMIF-product and/or the washed PMIF-product may be subjected to drying.

In an embodiment of the present invention the PMIF-product and/or the washed PMIF-product has a degree of esterification in the range of 10-55, such as in the range of 15-45, e.g. in the range of 20-40, such as in the range of 30-40.

In an embodiment of the present invention the PMIF-product and/or the washed PMIF-product has a degree of acetylation of 30 or less, e.g. a degree of acetylation of 25 or less, such as a degree of acetylation of 20 or less, e.g. a degree of acetylation of 15 or less, such as a degree of acetylation of 10 or less, e.g. a degree of acetylation of 5 or less.

The PMIF-product obtainable by the method according to the present invention may be capable of forming an unstable emulsion system.

In order to evaluate the stability of the system provided by the PMIF-product precipitates formed when left at rest are evaluated. These precipitates may be formed when the PMIF-product is mixed with a source of divalent cations, such as $Ca^{2+}$, water and oil. In an embodiment of the present invention PMIF-product precipitates when left at rest for a period of less than 2 hours, such as for a period less than 1 hour, e.g. for a period less than 30 minutes, such as for a period less than 15 minutes, e.g. for a period less than 10 minutes, such as for a period less than 5 minutes, e.g. for a period less than 2 minutes.

Mud

The suspension of the plant material, the PMIF-product or the washed PMIF-product may be subjected to a treatment giving a dry matter content above 15% providing a mud of said suspension of the plant material.

In the present context the term "mud" relates to a mixture of the plant material, the PMIF-product or the washed PMIF-product where the dry matter content has been significantly increased. Preferably, the dry matter content of the mud is above 15% and the mud becomes a heavily mixable mixture, which nevertheless can be pumped and kneaded. The high dry matter content and high water concentration allow one to manipulate the material in such a way as to solubilise the pectin or make a derivatisation of it simultaneous avoiding lost of pectin substances from the mud to the environment. In this manner the plant material may be subjected to different kind of treatments without extracting the pectin.

Preferably, the treatment giving a dry matter content above 15% (w/w) is selected from the group consisting of centrifugation, filtration, decanting, pressing (such as filter pressing or belt pressing), drying or any combination hereof.

In an embodiment of the present invention the dry matter content of the mud is above 15% (w/w), such as above 17% (w/w), e.g. above 20% (w/w), such as above 25% (w/w), e.g. above 35% (w/w), such as above 45% (w/w), e.g. above 50% (w/w).

In an embodiment of the present invention the mud provides an in situ system by swelling the plant material in the acidic aqueous solution substantially without suffer a loss of pectin from the mud. The part of the pectin that may dissolve from the swelled plant material will continue to be an integrated part of the mud.

In the present context the term "process" relates to the handling of the mud, such as stirring or mixing or kneading of added reagents.

PMSF

In an embodiment of the present invention the mud may be subjected to a first pH-neutralisation solution. After such a first pH-neutralisation the fibre-containing pectin product obtained is a plant material soluble fibre product (PMSF-product).

Preferably, the pH of the PMSF-product may be pH 2 or above, such as pH 3 or above, e.g. pH 4 or above, such as pH 5 or above, such as pH 6 or above, e.g. pH 7 or above, such as pH 8 or above, such as in the range of pH 3-9, e.g. in the range of pH 4-8, such as in the range of pH 5-8, e.g. in the range of pH 4-6, such as in the range of pH 4-5.

Such first pH-neutralisation solution may be accomplished by weak alkaline substances like different salts of hydrogencarbonates for instance sodium or potassium salts. Preferably, the first pH-neutralisation solution may be sodium citrate.

In an embodiment of the present invention the PMSF-product has a degree of esterification in the range of 10-55, such as in the range of 15-45, e.g. in the range of 20-40, such as in the range of 30-40.

In yet an embodiment of the present invention the PMSF-product has a degree of acetylation of 30 or less, e.g. a degree of acetylation of 25 or less, such as a degree of acetylation of 20 or less, e.g. a degree of acetylation of 15 or less, such as a degree of acetylation of 10 or less, e.g. a degree of acetylation of 5 or less.

The temperature during the step of subjecting the mud to the first neutralisation solution should be below 80° C., such as below 70° C., e.g. 60° C. or below, such as 50° C. or below, e.g. 40° C. or below, such as 30° C. or below, e.g. 25° C. or below, such as in the range of 0-80° C., e.g. in the range of 0-70° C., such as in the range of 0-60° C., e.g. in the range of 0-50° C., such as in the range of 10-40° C., e.g. in the range of 15-35° C., such as in the range of 20-30° C.

The PMSF-product may be capable of forming a stable emulsion system. Preferably, the PMSF-product may be capable of emulsifying at least 5% (w/w) oil, such as at least 10% (w/w) oil, e.g. at least 20% (w/w) oil, such as at least 30% (w/w) oil, e.g. at least 40% (w/w) oil, such as at least 50% (w/w) oil, e.g. at least 60% (w/w) oil.

The system provided by the PMSF-product may not form any precipitates when left to rest. This effect of precipitation may be evaluated when the PMSF-product is mixed with a source of divalent cations, such as $Ca^{2+}$, water and oil. In an embodiment of the present invention PMSF-product form no precipitates when left at rest for a period of more than 2 minutes, such as for a period of more than 5 minutes, e.g. for a period more than 10 minutes, such as for a period of more than 15 minutes, e.g. for a period more than 30 minutes, such as for a period of more than 45 minutes, e.g. for a period more than 60 minutes, such as for a period of more than 2 hours, e.g. for a period more than 5 hours, such as for a period of more than 10 hours, e.g. for a period more than 24 hours, such as for a period of more than 5 days, e.g. for a period more than 10 days.

The PIMF-product, washed PIMF-product, or the PMSF-product obtainable by the method according to the present invention may be different from other known pectin products. One distinct feature between the isolated pectin products according to the present invention and other known pectins may be the degree of blockiness.

In the present context the term "degree of blockiness" relates to the distribution of the galacturonic acid groups along the pectin molecule. Blockiness refers to the property of acid groups being clustered together in blocks as opposed to being distributed relatively randomly along the polymer. When the acid groups are distributed randomly their individual negative charges are relatively weak. However, when the acid groups occur in block-wise fashion, the negative charges associated with the blocks are relatively large. For purposes of the present description, degree of blockiness is expressed as the amount of non-methylated galacturonic acid molecules (mono, di, and trimer) liberated by treatment with an endo polygalacturonase, as a percentage of the total number of non-esterified galacturonic acid molecules per gram of pectin.

The method for determining the degree of blockiness of the PIMF-product, washed PIMF-product, or the PMSF-product according to the present invention is the same at the one applied in WO 00/58367 and by Daas, P. J. H. et al. (1988) which both hereby are incorporated by reference.

In an embodiment of the present invention the PIMF-product, washed PIMF-product, or the PMSF-product has a degree of blockiness of 6% or less, preferably a degree of blockiness of 5% or less, e.g. a degree of blockiness of 4% or less, preferably a degree of blockiness of 3% or less, e.g. a degree of blockiness of 2% or less, preferably a degree of blockiness of 1% or less, e.g. a degree of blockiness of 0.5% or less.

In a further embodiment of the present invention the isolated pectin has a degree of blockiness of 6% or less, preferably a degree of blockiness of 5% or less, e.g. a degree of blockiness of 4% or less, preferably a degree of blockiness of 3% or less, e.g. a degree of blockiness of 2% or less, preferably a degree of blockiness of 1% or less, e.g. a degree of blockiness of 0.5% or less and a degree of esterification from 0-55%, such as from 0-50%, e.g. from 0-40%, such as from 2-30%, e.g. from 2-25%, such as from 5-30%, e.g. from 10-50%, such as from 30-55%, e.g. from 15-35%.

PMAF

In a preferred embodiment of the present invention the PMIF-product, the washed PMIF-product or the PMSF-product in the state of a mud may be further subjected to an alkaline treatment providing a pH of 10 or above, such as a pH of 11 or above, e.g. a pH of 12 or above, such as a pH of 13 or above, e.g. a pH of 14, before obtaining the fibre-containing pectin product providing a plant material activated fibre product (PMAF-product).

Preferably, the alkaline treatment may be provided by adding to the mud an alkaline reagent selected from the group consisting of ammonia or other low molecular amines, diamines or hydroxides of sodium, potassium and calcium or hydroxides of organic bases, such as tetramethylammonium-hydroxide, carbonates of sodium, potassium and alkaline salts of phosphates.

In an embodiment of the present invention the PMAF-product may have a degree of esterification (DE) of 40% or less, e.g. a degree of esterification of 30 or less, such as a degree of esterification of 25 or less, e.g. a degree of esterification of 20 or less, such as a degree of esterification of 15% or less, e.g. a degree of esterification of 10 or less, such as a degree of esterification of 5 or less, e.g. a degree of esterification of 1 or less, such as a degree of esterification of 0.

In another embodiment of the present invention the PMAF-product may have a degree of amidation (DA) of 40% or less, e.g. a degree of amidation of 30 or less, such as a degree of amidation of 25 or less, e.g. a degree of amidation of 20 or less, such as a degree of amidation of 15% or less, e.g. a degree of amidation of 10 or less, such as a degree of amidation of 5 or less, e.g. a degree of amidation of 1 or less, such as a degree of amidation of 0.

Analogous to the degree of esterification, the degree of amidation is defined as the number of carboxamidated galacturonic acid units expressed as a percentage of all galacturonic acid units in the pectin molecule.

In particular, the PMAF-product may be characterised as having a degree of esterification in the range of 0-40, such as in the range of 0-30, e.g. in the range of 0-20, such as in the range of 0-10, e.g. in the range of 5-20, such as in the range of 10-15, such as in the range of 5-10, such as in the range of 0-8, e.g. in the range of 0-4, such as in the range of 0-2, e.g. in the range of 1-5, such as in the range of 2-3.

Alternatively, the PMAF-product may be characterised as having a degree of acetylation of 30 or less, such as a degree of acetylation of 20 or less, e.g. a degree of acetylation of 15 or less, such as a degree of acetylation of 10 or less, e.g. a degree of acetylation of 5 or less, such as a degree of acetylation of 0.

In an embodiment of the present invention the PMAF-product may be characterised as having a degree of esterification (DE) of 40% or less, e.g. a degree of esterification of 30 or less, such as a degree of esterification of 25 or less, e.g. a degree of esterification of 20 or less, such as a degree of esterification of 15% or less, e.g. a degree of esterification of 10 or less, such as a degree of esterification of 5 or less, e.g. a degree of esterification of 1 or less, such as a degree of esterification of 0 and/or a degree of acetylation of 30 or less, such as a degree of acetylation of 20 or less, e.g. a degree of acetylation of 15 or less, such as a degree of acetylation of 10 or less, e.g. a degree of acetylation of 5 or less, such as a degree of acetylation of 0 and/or a degree of amidation (DA) of 40% or less, e.g. a degree of amidation of 30 or less, such as a degree of amidation of 25 or less, e.g. a degree of amidation of 20 or less, such as a degree of amidation of 15% or less, e.g. a degree of amidation of 10 or less, such as a degree of amidation of 5 or less, e.g. a degree of amidation of 1 or less, such as a degree of amidation of 0.

In an embodiment of the present invention the PMAF-product may be subjected to a second pH-neutralisation solution. Preferably, the second pH-neutralisation solution may be an organic or mineral acid, More preferably, the second pH-neutralisation solution may be citric acid.

The temperature during the preparation of the PMIF-product, the washed PMIF-product, the PMSF-product or the PMAF-product may preferably be below 80° C., such as below 70° C., e.g. 60° C. or below, such as 50° C. or below, e.g. 40° C. or below, such as 30° C. or below, e.g. 25° C. or below, such as in the range of 0-80° C., e.g. in the range of 0-70° C., such as in the range of 0-60° C., e.g. in the range of 0-50° C., such as in the range of 10-40° C., e.g. in the range of 15-35° C., such as in the range of 20-30° C.

The plant material activated fibre product (PMAF-product) obtainable by the present invention may be capable of forming a stable gel in the presence of calcium ($Ca^{2+}$-ions) in systems comprising 25% (w/w) solids or less, such as 20% (w/w) solids or less, e.g. 15% (w/w) solids or less, such as 10% (w/w) solids or less, e.g. 5% (w/w) solids or less, such as 3% (w/w) solids or less, e.g. 1% (w/w) solids or less.

In an embodiment of the present invention the PIMF-product, the washed PIMF-product, the PMSF-product and the PMAF-product may be differentiated between each other by differences in viscosity. Thus, in aqueous systems enriched with divalent cations, such as calcium ions, under internal polymer setting conditions, the viscosity of the PIMF-product and the washed PIMF-product are significantly lower than the viscosity of the PMSF-product and the viscosity of the PMAF-product is significantly higher than the viscosity of the PMSF-product.

In another embodiment of the present invention the PIMF-product, the washed PIMF-product, the PMSF-product and the PMAF-product may be differentiated between each other by differences in gelling properties. Thus, in aqueous systems enriched with divalent cations, such as calcium ions, under internal polymer setting conditions the PIMF-product, the washed PIMF-product show substantially no gelling properties just as the PMSF-product has very weak gelling properties compared to the PMAF-product, which possess powerful gelling properties.

Isolation of Pectin from PMIF-PMSF-PMAF and the Isolated Pectin Product

The fibre-containing pectin products obtainable by the present invention may also be highly suitable starting materials for the production of purified pectin products. Such purified pectin products (as well as the fibre-containing pectin products as such) may proved surprisingly high gel strengths and viscous giving properties surpassing those of conventionally provided pectin.

Thus, according to the present invention a pectin product may be provided by the following method:
 (i) providing a fibre-containing pectin product according to the present invention,
 (ii) adding an extraction medium to the fibre-containing pectin product providing an extraction suspension,
 (iii) adjusting the pH of the extraction suspension to a pH in the range of 1-12,
 (iv) adjusting the temperature of the extraction suspension to a temperature in the range of 0-120° C., and
 (v) isolating the pectin product from the aqueous phase of the extracting medium.

In an embodiment of the preset invention the extraction medium may have a pH in the range of 1-6, such as in the range of 2-6, e.g. in the range of 2-5, such as in the range of 3-5, e.g. in the range of 4-5.

The temperature during the extraction process may be in the range of 40-100° C., such as in the range of 60-80° C.

In an embodiment of the present invention the fibre-containing pectin product may be subjected to a concentration procedure prior to isolation of the pectin.

After the pectin has been liberated from the fibre-containing pectin product the pectin product may be isolated by any known method such as precipitation, centrifugation, filtration, chromatography optionally followed by drying.

In yet an embodiment of the present invention the isolated pectin has a degree of esterification from 0-55%, such as from 0-50%, e.g. from 0-40%, such as from 2-30%, e.g. from 2-25%, such as from 5-30%, e.g. from 10-50%, such as from 30-55%, e.g. from 15-35% and/or a degree of amidation of not more 50%, such as not more than 40%, e.g. not more than 30%, such as not more than 25%, e.g. not more than 20%, such as not more than 10%, e.g. not more than 5%, such as not more than 2%, e.g. not more than 1%, such as 0.

The Dietary Fibre Product

The PIMF product, PMSF product, PMAF product or the isolated pectin product have shown to be effective as a dietary fibre product. Therefore, the method according to the present invention may be suitable for the preparation of a dietary fibre product.

In the present context the term "dietary fiber product" relates to the indigestible portion of plant foods that move food through the digestive system, absorbing water. Chemically, dietary fiber products comprises non-starch polysaccharides and generally the dietary fiber products may comprise several different plant components such as cellulose, lignin, waxes, chitins, pectins, beta-glucans, inulin and oligosaccharides.

One advantage of dietary fiber products may be that they promote the growth of microorganisms in the intestine and the dietary fiber products are not digested in the stomach, but rather fermented by the flora present in the intestine. This causes the dietary fiber products to act as a pre-biotic.

In the present context the term "pre-biotic" relates to a category of functional food products, defined as: Non-digestible food ingredients that beneficially affect the host by selectively stimulating the growth and/or activity of one or a limited number of bacteria in the colon or intestine, and thus improve host health. Thus, the dietary fiber products may be characterised as being a pre-biotic food product and/or a functional food product.

The pre-biotic effect obtainable by the present invention may influence the immune system assisting in fighting various diseases. However, the pre-biotic effect is not necessarily just for the treatment of a disease it may also have the effect of a prophylaxis treatment.

In an embodiment of the present invention the dietary fibre product may be a plant material fibre product. Preferably, the plant material fibre product may be the PMIF product, the PMSF product, the PMAF product, the isolated pectin product, as defined herein or any combination hereof.

Preferably the dietary fibre product may be obtained from a plant material selected from the group consisting of potato, sugar beet, pomace residues from apples, peels or pulp from citrus fruits, such as lemon, orange, mandarin, lime, grapefruit, tobacco, cacao, sun flower, pumpkin, mango, tomato and Aloe Vera or pulp thereof, in particular the plant material is selected from potato pulp and/or sugar beet pulp.

In an embodiment of the present invention the dietary fibre product (as well as the PMIF product, the PMSF product, the PMAF product and the isolated pectin product) may comprise a reduced content of glycoalkaloids relative to conventionally produced dietary fibre products. Preferably, the content of glycoalkaloids may be reduced by at least 5% (w/w), such as at least 10% (w/w), e.g. at least 20% (w/w), such as at least 50% (w/w), e.g. at least 75% (w/w), such as at least 90% (w/w), e.g. at least 95% (w/w), relative to conventionally produced dietary fibre products.

In the present context the term "glycoalkaloids" relates to a family of poisons compounds found in species of the nightshade family. A notable example of glycoalkaloids is solanine, which is found in potatoes. Glycoalkaloids may be bitter tasting, and may produce a burning irritation in the back of the mouth and side of the tongue when eaten. Symptoms of poisoning include diarrhea and vomiting, therefore, it may be of interest to limit the content of glycoalkaloids in food products.

In an embodiment of the present invention the PMIF product, the PMSF product, the PMAF product, the isolated pectin product or a combination hereof may be subjected to a splitting treatment wherein the PMIF product, the PMSF product, the PMAF product, the isolated pectin product or a combination hereof are divided (by the action of the splitting treatment) into smaller fragments of the PMIF product, the PMSF product, the PMAF product and the isolated pectin product resulting in different dietary fibre fractions comprising smaller dietary fibre products. Preferably the splitting treatment involves the action of an enzyme or a mixture of enzymes.

In an embodiment of the present invention the dietary fibre products comprises one or more dietary fibre fractions.

In an embodiment of the present invention the dietary fibre products according to the present invention may be added to a food product.

The Food Product

A common strategy for reducing the risk of overweight and obesity has been to reduce the average energy intake by lowering the dietary fat intake. Dietary fat is a major determinant for energy density of the diet and thereby for energy intake. A reduction in the daily consumption of fat concurrently, with an increase in the consumption of foods rich in complex carbohydrates, is part of the dietary recommendations in many countries.

An additional strategy may be to consume foods with a low digestibility. It is well established that the dietary fibre content of the diet is an important determinant of the digestibility of energy and energy-contributing macro-nutrients. It has been suggested that increasing amounts of dietary fibres in the food promotes satiety and thereby reduces energy intake, and decreases transit time of ingested food in the intestinal tract.

In an embodiment of the present invention a food product may be provided comprising a plant material fibre product, such as the PMIF product, the PMSF product, the PMAF product, the isolated pectin product, the dietary fibre product as defined herein or any combination hereof.

In a further embodiment of the present invention the food product may be selected from the group consisting of beverages, nutritional bar, a snack bar, a milk product (such as yoghurt, butter, cream, butter milk, yoghurt, junket, ice cream, cheese or combinations thereof), a baked product (such as bread, rye bread, biscuit, tea-biscuit, cracker, piecrust, pâté, patty and combinations thereof), a vegetable product, a meat product (such as liver paste, sausages, meatballs, beef burger, fish cake and combinations thereof), cereals, dressing e.g. for salads, a semi-manufactured product and combinations thereof.

The food product according to the present invention may be in the form of a semi-manufactured product. In the present context the term "a semi-manufactured product" relates to food products not ready to be eaten.

Technical Preparations

The products obtained according to the present invention may be a plant material insoluble fibre product (PMIF-product), a washed plant material insoluble fibre product (washed PMIF-product), a plant material soluble fibre product (PMSF-product), a plant material activated fibre product (PMAF-product) and/or a purified pectin product.

The products according to the present invention may have technical properties which immediately allow technical applications within various fields. The unsurpassed gel strength, viscosifying and emulsifying properties of the product make it suitable for, e.g. encapsulation of, e.g., easily volatile lipid and/or water-soluble aromatic and colouring agents. A property that can be used in the production of foods and feeds, as well as within the pharmaceutical and cosmetic industries, is e.g. encapsulating micronutrients, flavouring agents, vitamins, etc. The pectin products of the present invention are thus useful in the production of solid and liquid pharmaceutical compositions, including, e.g., tablets, suspensions, emulsions, etc. and as components in cosmetic products, such as perfumes, creams, and lotions, etc.

Under certain production conditions, the product of the invention generates a protective film around the agent(s) desirably to be protected from, e.g., oxygen, light, heat, etc. Alternatively, the agent desirably to be protected may be embedded in an encapsulation gel based on the present product.

Furthermore, the product may be applicable as a structuring agent by direct addition and/or by restructuring of components in foods and feeds. In feeds, e.g., by the restructuring of residual meat as chunks, as a viscosifying agent in gravies, gel-forming agents together with meat and bone meal and as a structuring component in dry feed products under low-pressure extrusions. Furthermore, the addition of the product will increase the autoclave stability of the feed products and the vigorous emulsifying effect may prevent fat leakage during autoclave treatment.

A particular utilization of the technical properties characterizing the pectin products of the invention is to use them in tobacco products, e.g., as a partial replacement for tobacco or as a technical aid when processing tobacco leaves or for the encapsulation of tobacco and nicotine. Moreover, the addition of pectin products of the invention to tobacco products will be directly structuring and/or will be useable when restructuring the tobacco products. Pectin products of the invention are easily suspended in water in high concentrations and may, depending on the activation degree of the product, be handled as a high viscous and sticky solution with high dry matter percentage. For the same reason, tobacco material may be restructured and stuck together by infusion of such a suspension prior to drying. The presence of a pectin product in the finished tobacco products has a water-binding effect and thus prevents drying to an unacceptable level. Any other tobacco ingredients may be dissolved, or form salt in the polymer mixture, and be mixed with the different pectin products, such as the PIMF-product, the washed PIMF-product, the PMSF-product or the PMAF-product. It should be noted that the above aroma-protecting properties, which are characteristic of pectin products of the invention, may also be applied for protecting aroma and flavour components in tobacco.

It should be noted that, according to the present invention, embodiments and features described in the context of one of the aspects of the present invention also apply to the other aspects of the invention.

Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The following examples are included to demonstrate particular embodiments of the invention. However, those of skill in the art should, in view of the present disclosure, appreciate that many changes can be made in the specific embodiments which are disclosed and still obtain a like or similar result without departing from the spirit and scope of the invention. The following examples are offered by way of illustration and are not intended to limit the invention in any way.

The invention may be described in more detail in the following non-limiting examples.

Example 1

Manufacture of a PMSF Product from Potato Plant Material Comprising Pectin

Dried plant material comprising pectin from potato starch production which had a degree of esterification DE=47.1% and a degree of acetylation DAc=39.8% and a calcium content of 25.0 mmol/kg dry matter was treated as described below:

850.0 g of the above dried plant material was suspended in 30.0 liter ion exchanged water by means of an Ultra Turrax (UT) high speed homogenizer. Simultaneously with addition of the dried plant material an aqueous nitric acid solution (2024.0 g 11.8% [g $HNO_3$/100 g solution]) was added giving a final pH of 1.20. After 7 min treatment with UT-setting speed 4 at 7600 rpm the temperature was 13.6° C. and the suspension appeared highly viscous and foaming. The foam was discarded at ½ hour UT stirring whilst the temperature increased to 15.0° C. The suspension was filtered through a cloth and dewatered in a screw press device. The press cake was subsequently suspended under UT stirring in the same amount of ion-exchanged water and acidified with aqueous nitric acid addition (888.0 g 11.8%) to a final pH 1.29. Once more the suspension was filtered and pressed as described above and at last re-suspended in 25.0 liter ion-exchanged water. The pH was 2.14 in suspension and after filtration and dewatering the compressed cake of PMIF product was kept in a refrigerator overnight and processed further the next day.

3250.0 g of the PMIF product was placed in a meat-chopper and under constantly processing dried with hot air until dry matter content around 30% was achieved. The free flowing material was reacted with an aqueous ammonia-solution (75.0 g, 8.3%) under slow addition of the alkaline agent to a final pH 4.5 in the wet powder (10 g wet powder suspended in 200 g water). The material was dried in a hot-air heating fan at 60° C. over night and finally grinded to provide a dried PMSF product.

The dry matter content of the PMSF product is 90% and the yield was 490 g. Degree of esterification was DE 47.1% and degree of acetylation was DAc 39.8%. The calcium concentration was 2.50 mmol/Kg dry matter.

Example 2

Effect of Calcium Concentration on Emulsifying Properties of a PMSF Product 200 kg dried plant material from a potato starch production at 10% dry matter was suspended in ad 600 kg tap water containing 1.50 kg calcium hydroxide under vigorous stirring at temperature 15° C. for 50 minutes. The pH declined from 12.2 to 11.6 during that time. The suspension was left overnight and pressed the next day in a filter press (Flottwegg). After pressing and dewatering the material dry matter content was measured to 28% before storage in a deep-freezer. 5.00 kg of that material was later thawed and minced in a chopper while 55.0 g citric acid mono hydrate was slowly added. By that pH was adjusted to 4.5 in the final blend before drying in a hot-air heating fan at 60° C. The dried material was grinded through 1.0 mm and 0.5 mm sieves. The calcium concentration was 449.0 mmol/Kg dry matter.

4.0 g of the above calcium rich dried material was suspended in 110.5 g ion exchanged water under UT-homogenizing treatment according to the Russian formula described in example 11 and heated in a microwave oven until boiling. After cooling the suspension was almost without viscosity. 30.0 g vegetable oil was now added to the 114.5 g of suspension under vigorous high speed stirring and the mixture was left on its own for a few minutes. After standing the oil/water mixture separates in two distinct phases with no sign of oil/water-emulsion stability.

4.0 g of the same calcium rich dried material as above was exhaustively acid washed on a glass filter and transferred to a glass beaker holding 110.5 g ion exchanged water. The pH was now raised to 4.5 with a diluted aqueous ammonia solution under high speed stirring with Ultra Turrax equipment to provide a PMSF product as in example 1 having a calcium concentration of 3.28 mmol/Kg dry matter. Shortly after the beginning of stirring the suspension became highly viscous and 30.0 g vegetable oil was added to the 114.5 g of suspension while stirring. A white stable homogeneous creamy emulsion was a reality immediately after mixing. The emulsion was stable stored in a refrigerator for weeks.

Example 3

Manufacture of a PMAF Product from Potato Plant Material Comprising Pectin 850.0 g dried plant material from a potato starch production, which had a degree of esterification DE=47.1% and a degree of acetylation DAc=39.8% and a calcium content of 25.0 mmol/kg dry matter was suspended in 30.0 liter ion exchanged water by means of an Ultra Turrax (UT) high speed homogenizer. The treatment with nitric acid and water and isolation of the press cake was as described in example 1 and the resulting PMIF product had a final pH of 2.29 before start of the activation process. The material was split in halves of each 3750.0 g was placed in a meat-chopper under constantly processing and dried with hot air until dry matter content around 23%-27% was achieved. The free flowing material resulting from the drying step was reacted with a solution of sodium hydroxide 9% (g NaOH/100 g solution) with slow addition of the alkaline agent to the wet powder. The pH was raised to 12.2 in the material at a temperature of 38° C. by adding 159.2 g aqueous sodium hydroxide solution during 12 minutes of high speed chopping. Reducing of the speed of the chopper one hour treatment was carried out until pH has fallen to 12.0. Nitric acid solution (330.0 g 12.4%) was added until pH has declined to 4.8. The material was dried in a hot-air heating fan at 60° C. over night and finally grinded to a fine powder to provide a PMAF product.

The PMAF product had a degree of esterification (DE) of almost zero, just as the degree of acetylation (DAc) was below the measurable range. The calcium concentration was 2.7 mmol/Kg dry matter.

Example 4

Optimized Manufacture of a PMAF Product from Potato Plant Material Comprising Pectin, Reducing Use of Base and Acid The remaining material from example 3 (3750.0 g) was treated in the same way as in the above example 3, but at a lower level of sodium hydroxide consumption. 94.0 g sodium hydroxide was added during 8 minutes of high speed chopping while pH increased to pH 11.6 in the material. After one hour reaction time at 38° C. the pH has decreased to pH 10.0. An aqueous nitric acid solution (91.1 g 12.4%) was added until pH had decreased to pH 5.0. The material was dried in a hot-air heating fan at 60° C. over night and finally grinded to a fine powder providing a PMAF product.

The sample was tested using the Russian Formula described in example 11 and displayed excellent gel strength indicative of low DE, DAc and calcium concentration, as mentioned in example 2. The calcium concentration was 2.72 mmol/Kg dry matter. The gels contain soluble and insoluble fibres and the pH is around 3.0.

Example 5

Manufacture of a PMSF Product from Potato Plant Material Comprising Pectin with Addition of NovoShape™ to Decrease the Degree of Esterification 5.0 kg of fresh plant material directly from a potato starch production having a calcium concentration of 25.0 mmol/Kg dry matter, a DE of 47.1% and a DAc of 39.8% was suspended in 20.0 liter of tap water and pH was adjusted to pH 1.3 with 30% aqueous nitric acid under UT stirring. The acid treated plant material was isolated as described in example 1 and re-suspended and washed one time with ion exchanged water giving pH 2.2 in the pressed material. The pH was adjusted to pH 4.5 using 50.0 g calcium chloride dihydrate was added and the temperature was raised to 34.6° C. 20.0 ml of NovoShape™ was dosed to the suspension under gentle stirring. After 15 minutes the material was isolated in a cloth as described in example 1 and dewatered in a hydraulic press to provide a PMSF product.

The dry matter content of the PMSF product was 29.7% after hydraulic pressing. The degree of esterification DE was 21%.

Example 6

Manufacture of a PMSF Product from Lemon Peel Plant Material Comprising Pectin The DE of naturally occurring lemon peels are around 70%, and it may be reduced before subjected to the method of the present invention. One method of reducing the DE may be as described in WO05/003178, but other methods could be used, e.g. enzymatic degradation.

1.60 kg dried plant material from lemon peels having a calcium concentration of 245.2 mmol/Kg dry matter, a DE of 70% and a DAc of 0% was suspended in 15.0 kg tap water and 7.0 kg crushed ice with a content of 360.0 g sodium chloride and 132.0 g calcium chloride dihydrate. The peel material was swollen under gentle stirring for 30 minutes at −1.5° C. After that 72.0 g calcium hydroxide was added cautiously to the suspension by means of which the calcium hydroxide powder was distributed homogeneous within one minute in the slurry. The reaction was performed at −1.5° C. and was stopped after 16 minutes by addition of 30% aqueous nitric acid to pH 1.0. After 11 minutes of acid treatment the material was isolated on a cloth and pressed in a hydraulic device to 16% dry matter. The acid wash was repeated twice with 20.0 liter water to pH 1.3 and finished by washing two times with the same volume of ion exchanged water without extra acid addition. The pH in the final PMIF product was 2.4. Under the washing process the acidic suspension was UT-treated at high speed stirring.

The resulting pressed PMIF product had dry matter content 16.0%, degree of esterification was DE=42.8%, and the calcium concentration was 85.7 mmol/Kg dry matter.

4.0 kg of the above mentioned material was carefully chopped in a meat chopper and dried to 2.9 kg with a hair dryer throughout 45 minutes treatment. 433.0 g of 10% aqueous sodium hydroxide was added slowly under continuous chopping during 27 minutes mixing-time and the chopping was continued for 60 minutes. The material was dried until a fine fluent powder with no lumps was achieved, and was further dried in an oven and grinded to provide a PMSF product.

The pH of a 1% suspension was 6.0, degree of esterification was DE=12.8% and the calcium concentration was 87.5 mmol/Kg dry matter. The sample was and displayed excellent gel strength when measured according to the Russian Formula of example 11 indicative of low DE (and DAc) as mentioned in example 2.

Also using the Russian Formula, in a similar experiment after the beginning of stirring, where the suspension became highly viscous, 30.0 g vegetable oil was added to the 114.5 g of suspension while stirring. A white stable homogeneous creamy emulsion was formed during mixing. The emulsion was stable stored in a refrigerator for 2 weeks as in example 2.

In a third experiment otherwise following the Russian formula, 50 mg sodium hexametaphosphate was added to the creamy white emulsion and further UT-treated. Afterwards 250 mg calcium sulfate dihydrate was added under high speed stirring. The emulsified suspension was heated in a micro wave oven for a few minutes. After cooling a white emulsified gel of high gel strength and stability was achieved.

Example 7

Manufacture of a PMSF Product from Grinded Tobacco Plant Material Comprising Pectin Dried plant material consisting of tobacco stems having a calcium concentration of 463.7 mmol/Kg dry matter, a DE of 20.2% and a DAc of 11.8% was grinded through 0.2 mm sieves. 742.5 g of the grinded plant material was suspended in 10.0 liter of ion exchanged water. Under gentle stirring with a paddle 560.6 g of aqueous sodium hydroxide solution (10%) was added and the reaction continued 2 hours and 36 minutes. During that time interval the pH declined from pH 12.20 to pH 11.84 and the temperature increased from 15.3° C. to 18.5° C. Diluted aqueous nitric acid (20.9%) was added and pH was brought down to 1.09 in the suspension. The activated material was isolated on a cloth and dewatered as described above in a screw press.

The press cake was suspended in 5.0 liter ion exchanged water and pH taken down to 1.22 with diluted nitric acid. After filtration another acid wash carried out at pH 1.11. The solid material was isolated as above and washed again three times giving a pH in the last wash around pH 2.3. Now the material was isolated on a cloth again and pressed to dry matter content of 30.7%, thereby providing a PMIF product based on grinded tobacco plant material with very low DE an DAc (less than 5%).

The wet material was placed in a meat chopper and aqueous sodium hydroxide solution (10%) was added under high speed chopping. 199.0 g aqueous sodium hydroxide solution was dosed until pH was 5.4 in the paste. The material was dried in a hot-air heating fan at 60° C. for 300 minutes and finally grinded to a fine powder to provide a PMSF product.

The gel strength of the resulting PMSF product having a lowered calcium concentration (less than 150 mmol/Kg dry matter) very low DE and DAc (less than 5%) was determined according to the Russian formula (see example 11) and showed that the gel strength was very high.

Example 8

Manufacture of a PMSF Product from Whole Tobacco Plant Material Comprising Pectin Dried plant material consisting of tobacco stems (1500.0 g) having a calcium concentration of 463.7 mmol/Kg dry matter, a DE of 20.2% and a DAc of 11.8% was suspended in 20.0 liter of ion exchanged water at temperature of 12.6° C. Under gentle stirring with a paddle 1000.0 g of aqueous sodium hydroxide solution (10%) was added and the reaction continued for 45 minutes. During that time interval the pH declined from pH 12.30 to pH 11.76 and the temperature increased from 12.6° C. to 13.8° C. The activated material was isolated on a cloth and dewatered as described above in a screw press during 20 minutes. The press cake was suspended in 20.0 liter ion exchanged water and pH brought down to 1.30 with aqueous nitric acid (30%). After filtration and pressing an acid wash was carried out at pH 1.09 in 20.0 liter ion exchanged water. The same procedure was repeated at pH 1.30 followed by a simple water wash with 20 liter ion exchanged water. The pH was 2.3 in the wash water and the washed material was pressed to 27.7% dry matter providing a PMIF product base on whole tobacco plant material.

The wet material was placed in a meat chopper and 500.0 g aqueous ammonia solution (2%) was slowly added under high speed chopping until pH was 4.6 in the homogeneous paste. The material was dried in a hot-air heating fan at 60° C. over night and finally grinded to a fine powder, resulting in a PMSF product.

The gel strength of the PMSF product determined according to the Russian formula (see example 11) was extremely high. The calcium concentration was 127.7 mmol/Kg dry matter and the DE and DAc were very low (less than 5%).

Example 9

Manufacture of a PMSF Product from Whole Tobacco Plant Material Comprising Pectin Without Initial Base Treatment Dried plant material consisting of tobacco stems (1500.0 g) having a calcium concentration of 463.7 mmol/Kg dry matter and a DE of 20.2% and a DAc of 11.8% was suspended in 20.0 liter of ion exchanged water at temperature of 13.8° C. Under gentle stirring with a paddle 1000.0 g of aqueous nitric acid solution (30%) was added and the mixture was stirred continuously for 30 minutes. During that time interval the pH was held at 1.05 at temperatures around 14° C. The acid treated material was isolated on a cloth and dewatered in a screw press during 20 minutes time. The press cake was again suspended in 20.0 liter ion exchanged water and pH brought down to 1.05 with 647 g of aqueous nitric acid (30%) and held there for 20 minutes under intermittent UT treatment. After filtration and pressing another acid wash was carried out at pH 1.10 in 20.0 liter ion exchanged water with 513 g of 30% aqueous nitric acid under UT treatment. The acid wash was followed by a simple water wash with 20 liters of ion exchanged water. pH was 1.9 in the wash water and the washed material was pressed to provide a PMIF product with unchanged DE and DAc).

The material was further processed at ambient temperature in a meat chopper at high speed by slow addition of 427.0 g aqueous ammonia solution (2%). After 30 min the pH was 4.5 in a 1% solution of chopped material. The material was dried in a hot-air heating fan at 60° C. over night and finally grinded to a fine powder to provide a PMSF product having a dry matter percentage of 90%, a calcium concentration of 14.8 mmol/Kg dry matter and DE and DAc as in the starting material.

Gel strength was determined according to the Russian formula (see example 11) and was shown to be high, but more elastic than the PMAF gel formulation described in example 10 below. The gel showed weak tendency to syneresis.

Example 10

Manufacture of a PMAF Product from Whole Tobacco Plant Material Comprising Pectin Dried plant material consisting of tobacco stems (1500.0 g) having a calcium concentration of 463.7 mmol/Kg dry matter and a DE of 20.2% and a DAc of 11.8% was treated as in example 9, and further processed at ambient temperature in a meat chopper at high speed by slowly addition of 380.0 g aqueous sodium hydroxide (10%) during 33 minutes. After 60 minutes of chopping the pH was 9.4 and the material was finally neutralized to pH 6.6 with a small amount of citric acid mono hydrate. The material was dried in a hot-air heating fan at 60° C. over night and grinded to a fine powder, thereby providing a PMAF product having a calcium concentration of 38.0 mmol/Kg dry matter, a DE of 7.8% and a DAc of 7.0%.

Gel strength was determined according to the Russian formula (see example 11) and was shown to be extremely high and even higher than the gel described in example 9, and the tendency to syneresis was also higher than in example 9. The calcium concentration was 38.0 mmol/Kg dry matter.

Emulsification properties like the ones described above was also observed with alkali treated tobacco stems registered both in example 8 and 9.

Example 11

The Russian Formula 4.00 g of the fibre containing pectin product, such as PMSF product obtained in example 2 and 5-9 or the PMAF product obtained in example 3, 4 and 10 was suspended in 110.5 g calcium depleted water with a content of 0.100 g sodium hexametaphosphate.

Ammonia of 25% concentrated solution is added until pH is 4.5 under high speed stirring by means of an Ultra Turrax machinery (UT).

When the suspension is highly viscous add 60 g sugar under UT treatment.

Weigh di-calcium hydrogen phosphate with two mol water in a weighing boat and transfer it quantitatively to the polymer solution by means of 5 g×2 ion exchanged water under UT-treatment.

Dissolve 2.2 g glucono-delta-lactone (GDL) in 12.5 g cold ion exchanged water and transfer the solution with 2.5 g ion exchanged water to the polymer solution under UT treatment.

Cast the viscous solution in plastic pans wrapped with tape.

After 24 hours the surplus of gel is removed by means of a cheese wire and the gel strength is measured.

The recipe with a content of 466 ppm calcium in the gel is described below:

| I) | |
|---|---|
| Fibre containing pectin product | 4.00 g (2%) |
| Sodium hexametaphosphate | 0.100 g |
| Ion exchanged water | 110.5 g |
| Sugar | 60.0 g (30%) |
| II) | |
| Glucono-delta-lactone | 2.2 g |
| Di-calcium hydrogen phosphate, 2H$_2$O | 0.410 g |
| Ion exchanged water | 25.0 g |
| Sum | 202.0 g |

Fraction I can be heated to the boiling point to enhance the solubility of fibre containing pectin product if necessary. The weight of the viscous solution just before casting the gel will be 200 g

REFERENCES

U.S. Pat. No. 5,567,462
WO 05/003178
WO 00/58367
Daas, P. J. H. et al., "Anal. Biochem., 257(2), pp 195-202 (1988)

The invention claimed is:

1. A method for providing a fibre-containing pectin product from a plant material, the method comprising the steps of:
   (i) providing a plant material comprising pectin, wherein the pectin has a degree of esterification of 55% or less,
   (ii) adding an acidic aqueous solution to the pectin containing plant material obtained in step (i), wherein the acidic solution does not comprise an organic solvent and does not comprise a salt, and providing a suspension of the plant material, wherein the suspended plant material provides an in situ system by swelling the plant material under conditions where the pectin is kept within the plant material and is not dissolved or extracted during the swelling, and
   (iii) obtaining the fibre-containing pectin product from the suspension provided in step (ii), wherein the plant material is allowed to swell in the acidic aqueous solution from 10 to 120 minutes and the plant material is substantially depleted of divalent cations during the swelling.

2. The method according to claim 1, wherein the plant material is depleted from divalent cations or substantially depleted from divalent cations by removing at least 10% w/w of the divalent cations naturally present in the plant material.

3. The method according to claim 1, wherein the content of divalent cations after addition of the acidic aqueous solution is 50 mmol/kg dry matter or less.

4. The method according to claim 1, wherein the fibre-containing pectin product obtained in step (iii) is a plant material insoluble fibre product (PMIF-product).

5. The method according to claim 4, wherein the PMIF-product is capable of absorbing water.

6. The method according to claim 4, wherein at least 0.1 g water is absorbed per gram PMIF-product.

7. The method according to claim 4, wherein the PMIF-product is depleted of the divalent cations.

8. The method according to claim 7, wherein the divalent cations include $Ca^{2+}$, $Mg^{2+}$, $Sr^{2+}$ or $Ba^{2+}$.

9. The method according to claim 7, wherein the content of the divalent cations is present in the PMIF-product and the content of the divalent cations after depletion is less than 40 mmol/kg dry matter.

10. The method according claim 7, wherein the PMIF-product is subjected to a wash that comprises water.

11. The method according to claim 10, wherein the PMIF-product and the wash are separated so as to provide a washed PMIF-product.

12. The method according to claim 11, wherein the separation is performed by filtration, centrifugation, decanting or a combination thereof.

13. The method according to claim 7, wherein the PMIF-product has a pH value in the range of pH 1-5.

14. The method according to claim 7, wherein the PMIF-product is subjected to drying.

15. The method according to claim 7, wherein the PMIF-product has a degree of esterification in the range of 10-55.

16. The method according to claim 7, wherein the PMIF-product has a degree of acetylation of 25 or less.

17. The method according to claim 1, wherein the suspension of the plant material is subjected to a treatment that provides a mud of the suspension of the plant material having a dry matter content above 15% w/w.

18. The method according to claim 17, wherein the treatment giving a dry matter content above 15% w/w is selected from the group consisting of centrifugation, filtration, decanting, and pressing or any combination thereof.

19. The method according claim 17, wherein the mud or the suspension of the plant material provides an in situ system by swelling the plant material in the acidic aqueous solution without extracting pectin from the mud.

20. The method according to claim 1, wherein the suspended pectin containing plant material is separated from the acidic aqueous solution.

21. The method according to claim 20, wherein the separation is performed by filtration, centrifugation, decanting, or pressing or a combination thereof.

22. The method according to claim 1, wherein the plant material is obtained from a native vegetable material in a fresh or dried state.

23. The method according to claim 1, wherein the plant material comprising pectin is selected from the group consisting of potato, sugar beet, apples, citrus fruits, tobacco, cacao, sun flower, pumpkin, mango, tomato and Aloe Vera or a pulp or peel thereof.

24. The method according to claim 1, wherein the plant material is subjected to comminution, pulverization, grinding, or tearing before the acidic aqueous solution is added.

25. The method according to claim 1, wherein the method is conducted at a temperature below 80.degree. C.

26. A method for providing a fibre-containing pectin product from a plant material, the method comprising:
   (i) providing a plant material comprising pectin, wherein the pectin includes a degree of esterification of 55% or less;
   (ii) adding an acidic aqueous solution to the pectin, wherein the acidic solution does not comprise an organic solvent and does not comprise a salt having a divalent cation, and providing a suspension of the plant material, wherein the suspended plant material provides an in situ system by swelling the plant material under conditions where the pectin is kept within the plant material and is not dissolved or extracted during the swelling; and
   (iii) obtaining the fibre-containing pectin product from the suspension, wherein the plant material is allowed to swell in the acidic aqueous solution from 10 to 120 minutes and is substantially depleted of divalent cations during the swelling, and wherein the fibre-containing pectin product is a plant material insoluble fibre product (PMIF-product) depleted of the divalent cations.

27. The method according to claim 26, wherein the PMIF-product is capable of absorbing water.

28. The method according to claim 27, wherein at least 0.1 g water is absorbed per gram PMIF-product.

* * * * *